United States Patent [19]

Lai et al.

[11] Patent Number: 5,106,409
[45] Date of Patent: Apr. 21, 1992

[54] AZOLE DERIVATIVES OF SPIROHETEROCYCLES

[75] Inventors: Hoi K. Lai, Guelph, Canada; Robert A. Davis; Allen R. Blem, both of Cheshire, Conn.

[73] Assignees: Uniroyal Chemical Company, Inc., Middlebury, Conn.; Uniroyal Chemical Ltd., Elmira, Canada

[21] Appl. No.: 521,193

[22] Filed: May 9, 1990

Related U.S. Application Data

[62] Division of Ser. No. 191,932, May 9, 1988, Pat. No. 4,943,311.

[51] Int. Cl.$^5$ .................. A01N 43/653; C07D 249/08
[52] U.S. Cl. .......................................... 71/92; 47/57.6; 514/383; 548/262.2; 548/267.2; 548/267.8; 548/268.6
[58] Field of Search ........................... 514/383; 71/92; 47/57.6; 548/262.2, 267.8, 268.6

[56] References Cited

U.S. PATENT DOCUMENTS 4,160,838   7/1979   Van Reet et al. ....................... 71/92

*Primary Examiner*—Patricia L. Morris
*Attorney, Agent, or Firm*—Glenn E. Karta

[57] ABSTRACT

A compound having the structural formula

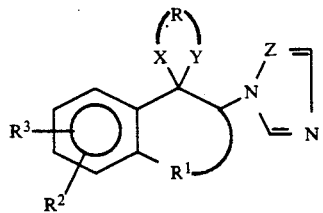

where
  R is $C_2$–$C_8$ alkylene having 2 to 4 carbon atoms linking X and Y;
  $R^1$ is $C_1$–$C_8$ linear or branched alkylene, $C_1$–$C_6$ oxyalkylene, $C_1$–$C_6$ thioalkylene or $C_1$–$C_6$ aminoalkylene;
  $R^2$ and $R^3$ are the same or different and are hydrogen, halogen, $C_1$–$C_8$ alkyl, $C_1$–$C_6$ alkoxy, $C_1$–$C_6$ alkylthio, $C_1$–$C_6$ alkylsulfonyl, phenyl, substituted phenyl, phenoxy, substituted phenoxy, cyano, nitro, —OCOR$^4$, —COOR$^5$, —CH$_m$Q$_{3-m}$ or —OCH$_m$Q$_{3-m}$,
  $R^4$ is $C_1$–$C_4$ alkyl;
  $R^5$ is hydrogen or $C_1$–$C_4$ alkyl;
  Q is halogen;
  X and Y are the same or different and are oxygen, sulfur, sulfinyl, sulfonyl or if one is NH, the other is sulfur;
  Z is nitrogen or CH; and
  m is 1, 2 or 3;
and physiologically acceptable salts thereof, is disclosed. A process for synthesizing the compound of this invention is also set forth. This process involves reacting a compound having the structural formula

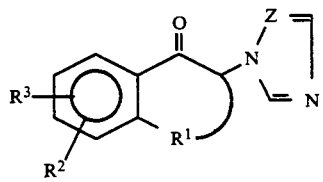

where $R^1$, $R^2$, $R^3$ and Z have the meanings given for the compound of this invention with a compound having the structural formula

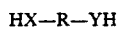

HX—R—YH where R, X and Y have the meanings given for the compound of the present invention. The compounds of this invention find utility as fungicides and plant growth regulants. Thus, the instant invention is also directed to processes for controlling fungi and regulating plant growth by utilizing effective amounts of the compound of the present invention to effectuate these goals. Finally, fungicidal and plant growth regulant compositions comprising effective amounts of the compound of this invention and carriers therefor is within the contemplation of the present invention.

8 Claims, No Drawings

AZOLE DERIVATIVES OF SPIROHETEROCYCLES

This is a division of application Ser. No. 07/191,932 filed May 9, 1988, now U.S. Pat. No. 4,943,311.

BACKGROUND OF THE INVENTION

1. Field of the Invention

The present invention is directed to a new class of azole derivatives of spiroheterocycles. More specifically, the present invention is directed to a new class of azole derivatives of spiroheterocycles useful as fungicides and plant growth regulants.

2. Background of the Prior Art

The control of phytopathogenic fungi is of great economic importance since fungal growth on plants or on parts of plants, i.e., fruits, blossoms, foliage, stems, tubers, roots, inhibits production of foliage, fruit or seed and the overall quality of the harvested crop.

Obviously, fungicides are well known in the art. However, the continuous economic toll, discussed above, taken by fungi establish a continuing need to develop new, more effective fungicides which possess curative, preventative and systemic action to protect cultivated plants. Those requirements must be accomplished without any adverse side effects, caused by the fungicide, on the plants to be protected.

Another need in the art is the continual requirement to develop new and effective plant growth regulants. As in the case of fungicides, there is a continuing need in the art to develop new and better plant growth regulants which regulate the growth of plants such that the difficulty and high cost of harvesting economically important plants is significantly reduced. Especially desirable are plant growth regulants that retard undesirable growth, such as excess foliage, of important crops without adversely affecting the yield and quality of the commercial crop to be harvested.

Compounds containing 1,3-dioxolane, 1,3-dithiolane and thiazolidine rings are known in the art. Such compounds are recited to possess spermicidal, antimicrobial, anticonvulsant and fungicidal properties depending upon their structure.

Thiazolidine compounds are disclosed in European Patent Application 92,158. The compounds of this disclosure are recited to possess fungicidal properties. The thiazolidine compounds of the '158 application are structurally distinguished from azole derivatives of spiroheterocycles.

U.S. Pat. No. 4,402,963 describes a class of dioxolanylalkyltriazole compounds which are not spiroheterocycles. These compounds are recited to possess important microbicidal properties. They are also set forth to be effective in combatting phytopathogenic fungi.

U.S. Pat. No. 4,359,475 is directed to a class of thioketal substituted N-alkyl imidazoles. These compounds, although azole derivatives, are not spiroheterocycles. The compounds of this disclosure are described as possessing utility as spermicides, as antimicrobials and as anticonvulsant agents.

Fundamentally, the compounds disclosed in the above three references are characterized by a following structural formula:

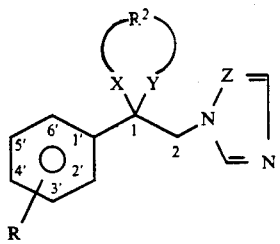

Azole derivative of spiroheterocycles have the generic formula as follows:

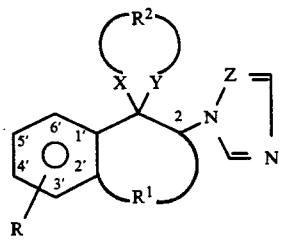

As the two above formulas establish, spiroheterocyclic compounds are characterized by a linkage between the 2-position bearing the azole moiety and the 2'-position of the aryl ring. The prior art disclosures provide no such linkage as indicated above.

Other references of interest include European Patent Applications 61,789 and 61,794. These two publications disclose the same class of compounds possessing the same utility, antimicrobial properties. The only difference between them is that the former application describes triazole derivatives and the latter application imidazole derivatives. Otherwise, the compounds of these two applications are identical. These compounds are far removed from azole derivatives of spiroheterocycles. It is noted that U.S. Pat. No. 4,483,865 is substantially identical with European Patent Application 61,794.

European Patent Application 29,355 is representative of another class of imidazole or triazole derivatives having utility as microbicidal agents. These azolyl ketals are not only distinguished from the two abovementioned European patent applications, but are also far removed from spiroheterocycles. The only similarity between the compounds of this European patent application and the compounds of the present invention is that they are said to be effective microbicidal agents, especially in combatting phytopathogenic fungi. U.S. Pat. No. 4,479,004 is substantially identical to European Patent Application 29,355.

Still another class of triazole derivatives, useful as an antimicrobial agent, as a fungicide and as a plant-growth regulant, 1-(beta-aryl)ethyl-1H-1,2,4-triazole ketals, are set forth in U.S. Pat. No. 4,079,062.

Arch. Pharmaz. (Weinheim, Ger.) 308, 94 (1975) discloses certain substituted benzoates, carbamates, and thiocarbamates as well as benzylic ethers prepared as derivatives of 2-imidazolyl-1-indanol and 2-imidazolyl-1-tetralol alcohols and found to be fungicidally active.

Finally, British Patent Application 2,098,607 discloses still another class of triazole or imidazole derivatives useful as agricultural fungicides as well as possessing antimycotic and/or anticonvulsive and anxiolytic agents in the pharmaceutical field. For example, compounds taught in this reference are alleged to provide effective control of parasitic fungi, for treating various forms of epilepsy and psychological diseases. These compounds are far removed from azole derivatives of spiroheterocycles.

The above remarks establish the need in the art for new and improved fungicides and plant-growth regulants. The above discussion, furthermore, emphasizes the uniqueness of azole spiroheterocycle compounds. Such compounds are not only not disclosed in the art, but no teaching of their use as fungicides or plant-growth regulants is made.

BRIEF SUMMARY OF THE INVENTION

The present invention is directed to a new class of azole derivatives providing excellent fungicidal and plant-growth regulant properties. Their structural uniqueness is based on the fact that the azoles are derivatives of spiroheterocycles. Such compounds are unknown in the art and have never been identified as having utility in the applications set forth herein.

In accordance with the present invention, a new class of compounds having the structural formula

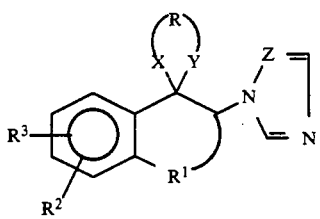

where
R is $C_2$–$C_8$ alkylene having 2 to 4 carbon atoms linking X and Y;
$R^1$ is $C_1$–$C_8$ linear or branched alkylene, $C_1$–$C_6$ oxalkylene, $C_1$–$C_6$ thioalkylene or $C_1$–$C_6$ aminoalkylene;
$R^2$ and $R^3$ are the same or different and are hydrogen, halogen, $C_1$–$C_8$ alkyl, $C_1$–$C_6$ alkoxy, $C_1$–$C_6$ alkylthio, $C_1$–$C_6$ alkylsulfonyl, phenyl, substituted phenyl, phenoxy, substituted phenoxy, cyano, nitro, —$OCOR^4$, —$COOR^5$, —$CH_mQ_{3-m}$ or —$OCH_mQ_{3-m}$;
$R^4$ is $C_1$–$C_4$ alkyl;
$R^5$ is hydrogen or $C_1$–$C_4$ alkyl;
Q is halogen;
X and Y are the same or different and are oxygen, sulfur, sulfinyl, sulfonyl or if one is NH, the other is sulfur;
Z is nitrogen or CH; and
m is 1, 2 or 3;
and physiologically acceptable salts thereof.

In another aspect of the present invention, a process for forming the compounds of the present invention is taught. In this process, an azole ketone having the structural formula

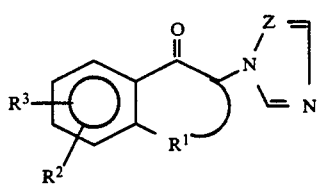

where $R^1$, $R^2$, $R^3$ and Z have the meanings given above, is reacted with a compound having the structural formula

HX—R—YH where X, Y and R have the meanings given above in the presence of an acid catalyst. An exception is made in the case where the meanings of X and Y are sulfinyl or sulfonyl. In those cases the spiroheterocycle having the structure of formula I following is reacted with m-chloroperoxybenzoic acid in a chlorinated hydrocarbon solvent, i.e., where X=SO, Y=SO and X=$SO_2$, Y=$SO_2$, compounds are prepared by oxidization of the spiroheterocycles. Also, in those cases where X is NH and Y is sulfur the azole ketone compound is reacted with an aminosubstituted reagent or its hydrochloride salt in the presence of a base catalyst.

In still another aspect of the instant invention, a process is provided for controlling fungi. In this process, a fungicidally effective amount of the compound of the present invention is applied to the locus to be protected.

In yet another aspect of the present invention, a fungicidal composition is disclosed. The fungicidal composition includes a fungicidally effective amount of the compound of the present invention and a carrier therefor.

In still yet another aspect of this invention, a process for controlling plant growth is set forth. In this process a plant growth regulant effective amount of the compound of the present invention is applied to the plant to be regulated.

In a final aspect of the subject invention, a plant growth composition is described. The plant growth composition of the present invention comprises a plant growth effective amount of the compound of the present invention and a carrier therefor.

DETAILED DESCRIPTION OF THE INVENTION

The compound of the instant invention has the following structural formula

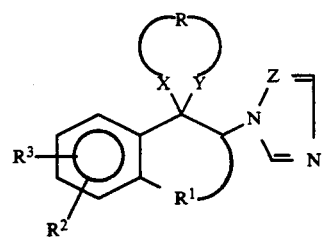

(I)

where
R is $C_2$–$C_8$ alkylene having 2 to 4 carbon atoms linking X and Y;
$R^1$ is $C_1$–$C_8$ linear or branched alkylene, $C_1$–$C_6$ oxalkylene, $C_1$–$C_6$ thioalkylene or $C_1$–$C_6$ aminoalkylene;
$R^2$ and $R^3$ are the same or different and are hydrogen, halogen, $C_1$–$C_8$ alkyl, $C_1$–$C_6$ alkoxy, $C_1$–$C_6$ alkylthio, $C_1$–$C_6$ alkylsulfonyl, phenyl, substituted phenyl, phenoxy, substituted phenoxy, cyano, nitro, —$OCOR^4$, —$COOR^5$, —$CH_mQ_{3-m}$ or —$OCH_mQ_{3-m}$;
$R^4$ is $C_1$–$C_4$ alkyl;
$R^5$ is hydrogen or $C_1$–$C_4$ alkyl;
Q is halogen;

X and Y are the same or different and are oxygen, sulfur, sulfinyl, sulfonyl or if one is NH, the other is sulfur;

Z is nitrogen or CH; and m is 1, 2 or 3;

and physiologically acceptable salts thereof.

More preferably, the compound of the present invention has the structural formula (I) where R is $-(CH_2)_n-$, $-CH_2CH(R^6)-$ or $-CH(CH_3)-CH(CH_3)-$;

$R^1$ is $C_1-C_3$ alkylene, $C_1-C_3$ oxyalkylene or $C_1-C_3$ thioalkylene;

$R^2$ and $R^3$ are the same or different and are hydrogen, halogen, $C_1-C_4$ alkyl, $C_1-C_4$ alkoxy, $C_1-C_4$ alkylthio, $C_1-C_4$ alkylsulfonyl, phenyl, substituted phenyl, phenoxy, substituted phenoxy, cyano, or nitro;

$R^6$ is $C_1-C_6$ alkyl;

X and Y are the same or different and are oxygen, sulfur, sulfinyl, sulfonyl or if one is NH, then the other is sulfur;

Z is nitrogen or CH; and n is 2 or 3;

and physiologically acceptable salts thereof.

The present invention is also directed to a process for the formation of a compound whose structural formula is (I). In one embodiment of the process of forming the compound having structural formula (I), a compound having the structural formula

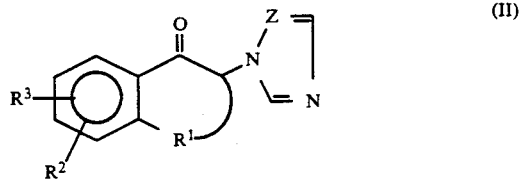

where $R^1$, $R^2$, $R^3$ and Z have the meanings given for the compound having structural formula (I) is reacted with a compound having the structural formula

HX—R—YH          (III)

where

R has the meanings given for structural formula (I); and

X and Y are the same or different and are oxygen or sulfur.

In this preferred embodiment, the compounds having the structural formulas (II) and (III) are reacted in the presence of an acid catalyst. Preferably, the acid catalyst is p-toluenesulfonic acid or methanesulfonic acid. In the preferred embodiment wherein the compound (III) is a dithiol (where X and Y are both sulfur) the reaction is preferably carried out neat in methanesulfonic acid. In another embodiment, the reaction occurs in the presence of a solvent mixture. In this embodiment, the preferred solvent mixture is a mixture of toluene and n-butanol.

In a second preferred embodiment, the process for synthesizing the compound having the structural formula (I) involves reacting a compound having the structural formula (II), where $R^1$, $R^2$, $R^3$ and Z have the meanings given for structural formula (I), with the compound having the structural formula (III) where one of X and Y is NH and the other sulfur. In this embodiment, the compound (III), the amino substituted compound or its hydrochloride salt, is reacted in the presence of a base catalyst. Preferably, the base catalyst is a trialkylamine, with triethylamine particularly preferred.

In yet a third preferred embodiment of the process of forming the compound having the structural formula (I), where X and Y are the same and are sulfinyl or sulfonyl, a compound having the structural formula (II), where $R^1$, $R^2$, $R^3$ and Z have the meanings given for the compound having the structural formula (I), is reacted with a compound having the structural formula (III), where X and Y are sulfur, in the presence of an acid catalyst. The preferred acid catalyst in this reaction is methanesulfonic acid. This results in the formation of a compound having the structural formula (I) where X and Y are sulfur.

This compound is then oxidized by reaction with m-chloroperoxybenzoic acid in a chlorinated hydrocarbon solvent, preferably dichloromethane or chloroform. To obtain the sulfinyl compound, two equivalents of m-chloroperoxy-benzoic acid are reacted per equivalent of compound (I) where X and Y are sulfur. That is, the molar ratio of compound (I) to m-chloroperoxybenzoic acid is 1:2. The temperature of this reaction is moderate, in the range of between about 0° C. and ambient temperature.

In order to synthesize the sulfonyl compound having the structural formula (I), the oxidation reaction of the compound having the structural formula (I) where X and Y are sulfur with m-chloroperoxybenzoic acid involves a molar ratio of m-chloroperoxybenzoic acid to compound (I) of at least 4:1. That is, at least 4 equivalents of m-chloroperoxybenzoic acid are used per equivalent of compound (I). More preferably, more than 4 equivalents of the m-chloroperoxybenzoic acid are reacted per equivalent of compound (I). The temperature of this reaction is the reflux temperature of the chlorinated hydrocarbon solvent in which this oxidation reaction occurs.

Those skilled in the art will be aware that the compounds of the present invention, made in accordance with the processes discussed immediately above, contain asymmetric carbon atoms. This is illustrated in formula (IV) below which depicts the compound of the present invention containing asymmetric carbon atoms at positions 2 of the spiroheterocyclic ring and at the 2'-position of the fused bicyclic ring.

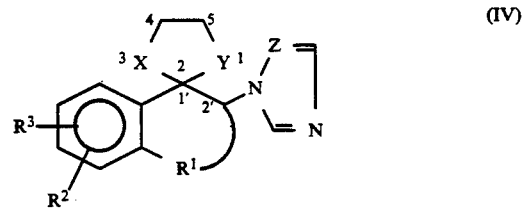

In addition, another asymmetric carbon atom exists at either the 4-position or 5-position of the spiroheterocyclic ring. This is illustrated in structural formula (V) below wherein $R^7$ and $R^8$ can be individually $C_1-C_6$ alkyl.

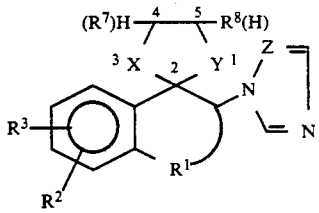

Stereoisomers depicted in structural formulas (IV) and (V) may or may not be separated. It is emphasized that not only are the separate isomers within the scope of the present invention, but mixtures of two or more of the stereoisomers, which may not necessarily be separated, are also within the scope of the present invention.

The triazole ketones having the structural formula (II) are generally novel. The triazole ketones having the structural formula (II) are prepared by the reaction of a haloketone having the structural formula

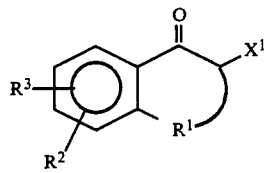

wherein $R^1$, $R^2$ and $R^3$ have the meanings given for the compound having the structural formula (I) and $X^1$ is chlorine or bromine, with an azole compound having the structural formula

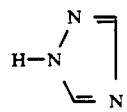

This method is analogous to that disclosed in P.A.J. Janssen et al, J. Med. Chem. 1969, 12, 784 whose disclosure is incorporated herein by reference.

In the case where $R^1$ is an alkylene containing an oxygen atom, by analogy, an alternate method of preparing triazole ketones having the structural formula (VII) is set forth in J. Heterocyclic Chem., 21, 311 (1984) wherein the preparation of imidazole ketones is disclosed. This disclosure is also incorporated herein by reference.

The haloketones defined by structural formula (VI) are generally known and may be prepared by known methods.

The compounds having the structural formula (I) are useful in a process for controlling phytopathogenic fungi. In this process a fungicidally effective amount of the compound having structural formula (I) where the meanings of R, $R^1$, $R^2$, $R^3$, $R^4$, $R^5$, $R^6$, Q, X, Y, Z, m and n are those given for the compound of structural formula (I) is applied to the locus under attack by said fungi.

In a first preferred embodiment, the method by which a fungicidally effective amount of the compound having structural formula (I) is applied to the plants to be protected from phytopathogenic fungi is by application of the compound having the structural formula (I) to the foliage of the plants to be protected. This compound is applied to the foliage in a concentration of 0.125 to 10 kilograms per hectare (kg/ha). More preferably, the embodiment wherein fungi are controlled in a process comprising applying a fungicidally effective amount of the compound having structural formula (I) entails applying 0.125 to 5.0 kg/ha of compound (I) to the foliage of the plants to be protected from said phytopathogenic fungi.

In the second preferred embodiment of the process for controlling phytopathogenic fungi, a fungicidally effective amount of the compound having the structural formula (I) is applied to the soil in which the plants to be protected from phytopathogenic fungi are grown. In this embodiment, the compound having the structural formula (I) is applied to the soil in which the plants to be protected are grown at a concentration of 10 to 500 mg/l. The exact dosage, within this concentration range, is dictated by the fungi to be controlled and the particular plants to be protected.

As those skilled in the art are aware, the first preferred embodiment of the process for controlling fungi is the foliage method. The second preferred embodiment is the systemic method of application. Either method may be utilized prior to infection or after fungi attack has begun.

Alternately, in yet another embodiment of the process of the present invention for controlling phytopathogenic fungi, the compound having the structural formula (I) may be applied to the seeds as a coating. This method provides plant protection from dangerous fungi by either chemotherapeutic means or systemic means or both. That is, the coating to the seed may protect the soil from infection by the fungi or may be taken up by the plant systemically to protect the plant from the fungal attack. In this seed coating method, the appropriate concentration of the compound having the structural formula (I) is in the range of between 5 and 75 grams of compound per 100 kg. of seed.

In still another aspect of the present invention, a process for regulating growth of a plant is provided. In this process a plant growth regulant effective amount of the compound having structural formula (I), where R, $R^1$, $R^2$, $R^3$, $R^4$, $R^5$, $R^6$, $R^7$, $R^8$, Q, X, Y, Z, m and n have the meanings given for compound (I), is applied to the plant whose growth is to be regulated.

Yet another important aspect of the present invention involves the disclosure of new fungicidal compositions. The fungicidal composition of the present invention comprises a fungicidally effective amount of the compound having the structural formula (I), where R, $R^1$, $R^2$, $R^3$, $R^4$, $R^5$, $R^6$, $R^7$, $R^8$, Q, X, Y, Z, m and n have the meanings given for compound (I), and a carrier therefor.

More preferably, the fungicidal composition comprises a fungicidally effective amount of the compound having structural formula (I), wherein the meanings of R, $R^1$, $R^2$, $R^3$, $R^4$, $R^5$, $R^6$, $R^7$, $R^8$, X, Y, Z, m and n have the preferred meanings for the compound having structural formula (I), and a carrier therefor.

In a final aspect of the present application a plant growth regulant composition is provided. This composition comprises a plant growth regulant effective amount of the compound having the structural formula (I), where R, $R^1$, $R^2$, $R^3$, $R^4$, $R^5$, $R^6$, $R^7$, $R^8$, Q, X, Y, Z, m and n have the meanings given for compound (I), and a carrier therefor.

More preferably, a plant growth regulant composition is disclosed which comprises a plant growth regulant effective amount of the compound having structural formula (I) wherein the preferred meanings of R, $R^1$, $R^2$, $R^3$, $R^4$, $R^5$, $R^6$, $R^7$, $R^8$, X, Y, Z, m and n are those given for the preferred embodiment of the compound having structural formula (I), and a carrier therefor.

The carrier employed in the fungicidal and plant growth regulant compositions may be a finely divided or granular organic or inorganic inert material. Among the inert carriers within the contemplation of this invention are attapulgate clay, sand, vermiculite, corncobs, activated carbon and mineral silicates such as mica, talc, pyrophyllite and clays.

In another preferred embodiment of carrier employed in the composition of this invention, the carrier comprises a solution. That is, the active agent, a compound whose structural formula is (I) is dissolved in a suitable solvent which acts as the carrier. Among the solvents, acting as carrier, within the contemplation of this invention are acetone, methanol, isopropanol, t-butyl alcohol, cyclohexanol, n-butyl alcohol, cyclohexanone, toluene, xylene, dioxane, dimethylformamide, dimethylsulfoxide, ethylene dichloride, diacetone alcohol, and N-methylpyrrolidone.

In still another preferred embodiment of the carrier utilized in the composition of the present invention, the carrier comprises a water emulsion. The water emulsion is prepared from a solution as described immediately above. To the solution is added a surface active agent. Surface active agents suitable for use in forming the emulsion of this invention are known to those skilled in the art. *McCutcheon's Detergents and Emulsifiers*, Allured Publishing Corp., Ridgewood, N.J. (1970); U.S. Pat. No. 2,514,916, Columns 2 to 4; and U.S. Pat. No. 2,547,734, Columns 3 and 4, provide detailed Examples of such surface active agents. The surface active agents may be anionic, non-ionic or cationic.

In still another embodiment of a carrier used in the composition of the present invention, the carrier is a dispersant. In this embodiment, the active agent, the compound having structural formula (I), is mixed with a dispersant. The dispersant includes a solvent of the type described above, one of the above-described surface active agents and water. The active agent is dissolved in the solvent to form a solution. The solvent is dispersed in the water with the aid of the surface active agent.

In still another embodiment of the carrier constituent of the composition of the present invention, the active compound, the compound having the structural formula (I), is premixed with an inert solid carrier which is added to a surface active agent and water to provide another form of dispersion type carrier within the contemplation of the composition of this invention.

The embodiment discussed immediately above, the disposal of the compound having the structural formula (I) on a solid inert carrier which is dispersed in the liquid to form a dispersion, may alternatively be employed in a non-liquid form. That is, the composition of this invention may take the form of dust, granules or a paste of a wettable powder. In these embodiments the active compound of this invention, the compound having the structural formula (I), is admixed with an inert solid carrier to form a solid composition. Thus, for example, in the embodiment wherein a powder is formed, the solid inert carrier is provided in powder form. In many such cases the inert carrier is a mineral silicate. The solid may be made wettable by the addition of a surface active agent, well known to those skilled in the art, and referred to in the above-recited references directed to surface active agents.

In a final embodiment of the carrier component of the composition of this invention, the carrier is an aerosol. To prepare an aerosol, the active compound is dissolved in a first solvent. This first solvent is conventional in the sense that although it is volatile it is not highly volatile. This solution is then admixed with a highly volatile solvent, a so-called liquid aerosol carrier. The aerosol carrier is liquid only under elevated pressure. At ordinary temperatures and at atmospheric pressure, the aerosol carrier is a gas. In a subembodiment of this preferred carrier, the aerosol carrier may itself be active. For example, the carrier may be an insecticide, a herbicide, a bactericide or the like.

Among the carriers discussed above, the carriers comprising solvents and emulsions are particularly preferred in the production of the fungicidal and plant growth regulant compositions of the present invention.

The following examples are given to illustrate the scope of the present invention. Because these examples are given for illustrative purposes only, the invention embodied herein should not be limited to the actual examples provided.

EXAMPLE 1

Preparation of
3',4'-Dihydro-2'-(1H-1,2,4-Triazol-1-yl)-Spiro-[1,3-Dioxolane-2,1'(2'H)-Naphthalene] (Compound No. 35)

A mixture of 10 g. 3,4-dihydro-2-(1H-1,2,4-triazol-1-yl)-1-(2H)-naphthalenone, 5.8 g. ethylene glycol and 11.5 g. p-toluenesulfonic acid was refluxed in a mixed solvent of 150 ml. toluene and 70 ml. n-butanol under a Dean-Stark [trademark] trap for 48 hours. The solvent was evaporated leaving a slurry which was taken up in dichloromethane and washed twice with 10% aqueous sodium hydroxide and once with water. The extract was dried in sodium sulfate, filtered and evaporated leaving an oily residue which crystallized on cooling to yield 1.5 g. of white crystals. These white crystals were 3',4'-dihydro2'-(1H-1,2,4-triazole-1-yl)-spiro-[1,3-dioxolane-2,1'(2'H)-naphthalene]. This compound had a melting point of 108° C.

EXAMPLE 2

Preparation of
7'-Chloro-3',4'-Dihydro-2-(1H-1,2,4-Triazol-1-yl)-Spiro-[1,3-Dithiolane-2,1'-(2'H)-Naphthalene]
(Compound No. 48)

To a stirred mixture of 2.7 g. 7-chloro-3,4-dihydro-2-(1H-1,2,4-triazol-1-yl)-1 (2H)-naphthalenone and 10 ml. methanesulfonic acid at ambient temperature was added 5 ml. ethanedithiol and the resulting mixture was allowed to react overnight. The reaction mixture was diluted with dichloromethane, neutralized with solid sodium bicarbonate and then washed thoroughly with 20% aqueous sodium hydroxide and water. The organic layer was dried over magnesium sulfate, filtered and evaporated to yield an oily residue.

The oily residue upon trituration with ethyl ether gave 1.2 g. of 7'-chloro-3',4'-dihydro-2-(1H-1,2,4-triazol-1-yl)-spiro-[1,3-dithiolane-2,1'-(2'H)-naphthalene]. This compound appeared as white crystals having a melting point of 156° C.–157° C.

EXAMPLE 3

Preparation of
2′,3′-Dihydro-3′-(1H-Imidazol-1-yl)-Spiro-[1,3-Dithiane-2′,4′(4H)-1-Benzopyran] (Compound No. 38)

In a manner analogous with Example 2, 4.3 g. of 2,3-dihydro-3-(1H-imidazol-1-yl)-4H-1-benzopyran-4-one was reacted with 9.2 g. of 1,3-propanedithiol in 20 ml. of methanesulfonic acid to yield 2.5 g. of white crystals.

The compound, 2′,3′-dihydro-3′-(1H-imidazol-1-yl)-spiro-[1,3-dithiane-2′,4′(4H)-1-benzopyran, had a melting point of 146° C.–148° C.

EXAMPLE 4

Preparation of
2′,3′-Dihydro-2′-(1H-1,2,4-Triazol-1-yl)-Spiro-[Thiazolidine-2,1′(1H)-Indene](Compound No. 46)

To a slurry of 6.3 g. 2,3-dihydro-2-(1H-1,2,4-thiazol-1-yl)-1H-inden-1-one in 75 ml. toluene and 75 ml. n-butanol was added 7.2 g. 2-aminoethanethiol hydrochloride and 6.4 g. triethylamine. The mixture was refluxed under a Dean-Stark [trademark] trap for 50 hours. After cooling, the formed precipitate was removed by filtration and the filtrate was washed with water, dried with sodium sulfate and concentrated to yield an oil. The oil was chromatographed on silica gel and eluted with ethyl acetate. This yielded 2.1 g. of white crystals. This material, having a melting point of 114°–117° C., was identified as 2′,3′-dihydro-2′-(1H-1,2,4-triazol-1-yl)-spiro-[thiazoladine-2-1′(1H)-indene].

EXAMPLE 5

Preparation of
3′,4′-Dihydro-2′-(1H-1,2,4-Triazol-1-yl)-Spiro-[1,3-Dithiane-2,1′(2′H-Naphthalene], 1,3-Dioxide (Compound No. 21)

To a solution of 3 g. 3′,4′-dihydro-2′-(1H-1,2,4-triazol-1-yl)-spiro-[1,3-dithiane-2,1′(2′H)-naphthalene] in 100 ml. dichloromethane at 0° C. was added, dropwise, 4 g. of 80–85% m-chloroperoxybenzoic acid in 50 ml. dichloromethane. After the addition was complete, the mixture was allowed to warm to room temperature and was stirred overnight. The solution was washed twice with 5% aqueous sodium bicarbonate and once with water. The organic extract was dried over sodium sulfate and evaporated to yield 2.6 g. of white crystals.

These crystals were identified as 3′,4′-dihydro-2′-(1H-1,2,4-triazol-1-yl)-spiro-[1,3-dithiane-2,1′(2′H-naphthalene], 1,3-dioxide, having a melting point of 95° C.–103° C.

EXAMPLE 6

Preparation of
3′,4′-Dihydro-2′-(1H-1,2,4-Triazol-1-yl)-Spiro-[1,3-Dithiolane-2,1′(2′H)-Naphthalene], 1,1,3,3-Tetroxide (Compound No. 15)

A solution was prepared by adding 100 ml. dichloromethane to 3 g. 3′,4′-dihydro-2′-(1H-1,2,4-triazol-1-yl)-spiro-[1,3-dithiolane-2,1′(2′H)-naphthalene]. Dropwise, 8.9 g. of 80–85% m-chloroperoxybenzoic acid in 100 ml. dichloromethane was added to this solution at room temperature. After the addition was completed, the mixture was refluxed for five hours. The reaction mixture was then washed twice with 10% aqueous sodium bicarbonate, once with water, dried with sodium sulfate and evaporated to yield 2.5 g. of product.

The product, 3′,4′-dihydro-2′-(1H-1,2,4-triazol-1-yl)-spiro-[1,3-dithiolane-2,1′(2′H)-napthalene], 1,1,3,3-tetroxide, had a melting point of 225° C.–226° C. (decomposed).

EXAMPLE 7

Preparation of Compound Nos. 1–14, 16–20, 22–34, 36, 37, 39–45 and 47

Compound Nos. 1–14, 16–20, 22–34, 36, 37, 39–45 and 47 were prepared in accordance with the procedures enumerated in Examples 1 to 6. These compounds are tabulated in Table I. Table I defines the compounds and characterizes them by their melting point. Compounds 35, 48, 38, 46, 21 and 15, prepared in accordance with the procedures of Examples 1 to 6, respectively, are included in the table for completeness.

Compound Nos. 7, 9, 10, 25 and 42–44 are oils at ambient conditions. These compounds, which cannot be characterized by melting point, were characterized by nuclear magnetic resonance (NMR) data. This NMR data is included in Table II which follows Table I.

EXAMPLE 8

Preparation of
3,4-Dihydro-2-(1H-1,2,4-triazole-1-yl)-1(2H)-Naphthalenone

To a mixture of 30 g. potassium carbonate, 15 g. 1,2,4-triazole and 250 ml acetonitrile at 40° C. was added a solution of 45 g. 3,4-dihydro-2-bromo-1(2H)-naphthalenone in 150 ml acetonitrile. The mixture was allowed to react for 5 hours at 40° C. and then at reflux temperature for 2 hours. The solid was removed by filtration and the filtrate concentrated to dryness leaving a solid residue. This was dissolved in dichloromethane and washed twice with water. The organic extract was dried over sodium sulfate and evaporated to give 42 grams of product having a melting point of 96°–98° C.

The above procedure is generally applicable to the synthesis of all azole ketones of structural formula (II) with $R^1$, $R^2$, $R^3$ and Z as defined herein.

TABLE I

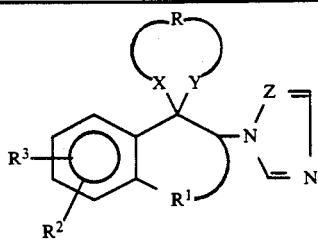

| Cpd. No. | X | Y | R | $R^1$ | $R^2$ | $R^3$ | Z | m.p., °C. |
|---|---|---|---|---|---|---|---|---|
| 1 | S | S | —CH$_2$CH$_2$— | CH$_2$ | H | H | N | 90 |
| 2 | SO$_2$ | SO$_2$ | " | " | " | " | " | 184–90 |
| 3 | S | S | —(CH$_2$)$_3$— | " | " | " | " | 126–8 |
| 4 | S | S | " | " | " | " | " | 197–9 (CH$_3$C$_6$H$_4$SO$_3$H) |
| 5 | SO$_2$ | SO$_2$ | " | " | " | " | " | 295–7 |
| 6 | S | S | —CH$_2$C(CH$_3$)H— | " | " | " | " | 185–8(HCl) |
| 7 | S | S | —CH$_2$C(C$_2$H$_5$)H— | " | " | " | " | oil* |
| 8 | S | S | —CH$_2$CH$_2$— | " | " | " | CH | 124–5 |
| 9 | S | S | —CH$_2$C(CH$_3$)H— | " | " | " | " | oil* |
| 10 | S | S | —CH$_2$C(C$_2$H$_5$)H— | " | " | " | " | oil* |
| 11 | S | S | —(CH$_2$)$_3$— | " | " | " | " | 100–3 |
| 12 | S | S | —CH$_2$CH$_2$— | —CH$_2$CH$_2$— | " | " | N | 98–9 |
| 13 | S | S | " | " | " | " | " | 105–6 (HNO$_3$) |
| 14 | SO | SO | " | " | " | " | " | 172–4 |
| 15 | SO$_2$ | SO$_2$ | —CH$_2$CH$_2$— | —CH$_2$CH$_2$— | H | H | N | 225–6 |
| 16 | SO$_2$ | SO$_2$ | " | " | " | " | " | 223–6 (CH$_2$C$_6$H$_4$SO$_3$H) |
| 17 | S | S | " | " | 5-OCH$_3$ | " | " | 137–9 |
| 18 | S | S | " | " | 6-OCH$_3$ | " | " | 136–40 |
| 19 | S | S | " | " | 7-OCH$_3$ | " | " | 112–4 |
| 20 | S | S | —(CH$_2$)$_3$— | " | H | " | " | 74–78 |
| 21 | SO | SO | " | " | " | " | " | 95–103 |
| 22 | SO$_2$ | SO$_2$ | " | " | " | " | " | 265–7 |
| 23 | S | S | —CH$_2$C(CH$_3$)H— | " | " | " | " | 146–54 |
| 24 | S | S | —CH$_2$C(C$_2$H$_5$)H— | " | " | " | " | 113–4 |
| 25 | S | S | —CH$_2$C(C$_2$H$_5$)H— (isomers) | " | " | " | " | oil* |
| 26 | S | S | —CH$_2$CH$_2$— | " | " | " | CH | 158–60 |
| 27 | S | S | —CH$_2$C(CH$_3$)H— | " | " | " | " | 103–5 |
| 28 | S | S | —(CH$_2$)$_3$— | " | " | " | " | 141–2 |
| 29 | SO | SO | —(CH$_2$)$_3$— | " | " | " | " | 100–5 |
| 30 | S | S | —CH$_2$CH$_2$— | —(CH$_2$)$_3$— | " | " | N | 95–7 |
| 31 | S | S | —(CH$_2$)$_3$— | " | " | " | " | 132–4 |
| 32 | S | S | —CH$_2$CH$_2$— | —(CH$_2$)$_3$— | H | H | CH | 130–3 |
| 33 | S | NH | —CH$_2$CH$_2$— | —CH$_2$— | " | " | " | 162–7 |
| Isomer B 34 | S | NH | " | —CH$_2$CH$_2$— | " | " | N | 99–101 |
| 35 | O | O | " | " | " | " | " | 108 |
| 36 | S | S | " | —OCH$_2$— | " | " | CH | 127–9 |
| 37 | SO | SO | " | " | " | " | " | 93–5 |
| 38 | S | S | —(CH$_2$)$_3$— | " | " | " | " | 146–8 |
| 39 | S | S | —CH$_2$CH$_2$— | —OC(CH$_3$)H— | " | " | " | 161–3 |
| 40 | SO | SO | " | " | " | " | " | 143–6 |
| Isomer A 41 | S | NH | " | —CH$_2$CH$_2$— | " | " | N | 120 |
| Isomer B 42 | S | S | —CH$_2$C(C$_2$H$_5$)H— | —OCH$_2$— | " | " | CH | oil* |
| Isomer B 43 | S | S | " | " | " | " | " | oil* |
| Mixture 44 | S | S | —CH$_2$C(CH$_3$)H— | " | " | " | " | oil* |
| Mixture 45 | S | NH | —CH$_2$CH$_2$— | —CH$_2$CH$_2$— | " | " | " | 105–112 |
| Mixture 46 | S | NH | " | —CH$_2$— | " | " | N | 114–117 |
| 47 | S | NH | " | —OCH$_2$— | " | " | CH | 155–158 |
| 48 | S | S | " | —CH$_2$CH$_2$— | 7-Cl | " | N | 156–157 |

*See Nuclear Magnetic Resonance (NMR) data in Table II.

TABLE II

Nuclear Magnetic Resonance (NMR) Data

Cpd. No. 7 (CDCl$_3$): δ 8.2 (H,s), 7.9 (1H,s), 7.2–7.8 (4H,m), 5.1–5.4 (1H,m), 3.7–4.3 (1H,m), 2.2–3.7 (4H,m), 1.4–2.0 (2H,m), 0.6–1.2 (3H,m)

Cpd. No. 9 (CDCl$_3$): δ 6.8–7.8 (7H,m), 4.7–5.0 (1H, broad t), 3.6–4.3 (H,m), 2.2–3.2 (4H,m), 1.0–1.4 (3H,m)

Cpd. No. 10 (CDCl$_3$): δ 6.9–8.0 (7H,m), 4.7–5.0 (1H, broad t), 2.3–4.3 (5H,m), 1.4–2.3 (2H,m), 0.7–1.3 (3H, 2 sets of t)

Cpd. No. 25 (CDCl$_3$): δ 8.4 (1H, sxs), 8.3 (1H, sxs); 7.9–8.3 (1H,m), 6.9–7.4 (3H,m), 4.7–5.1 (1H,m), 3.8–4.3 (1H,m), 2.3–3.4 (6H,m), 1.4–2.1 (2H,m), 0.8–1.2 (3H,m)

Cpd. No. 42 (CDCl$_3$): δ 7.65–8.10 (2H,m), 6.75–7.30 (5H,m), 4.45–4.85 (3H,m), 2.90–4.30 (3H,m), 0.80–2.20 (5H,m)

Cpd. No. 43 (CDCl$_3$): δ 7.70–8.10 (2H,m), 4.50–4.80 (3H,m), 2.80–4.25 (3H,m), 0.75–2.0 (5H,m)

Cpd. No. 44 (CDCl$_3$): δ 7.67–8.10 (2H,m), 6.70–7.40 (5H,m), 4.50–4.85 (3H,m), 2.20–3.30 (3H,m), 1.20–1.50 (3H,m)

EXAMPLE 9

Preparation of Fungicidal and Plant Regulant Compositions

The compounds prepared in Examples 1–7 (Compound Nos. 1–48) were formed into compositions. This was accomplished by dissolving 0.3 g. of each of the compounds in 10 ml. of acetone or other suitable solvent. Each of these solutions were treated with 1 to 2 drops of an emulsifying agent, such as Triton [trademark] X-100, and water was added to form an emulsion. The degree of dilution with water dictated by the desired concentration of the composition. The greater the quantity of water added the lower the concentration of the composition, reported in milligrams per liter (mg/l).

EXAMPLE 10

Control of Powdery Mildew Fungus (Systemic Root Uptake)

Each of the compounds prepared in accordance with Examples 1–7, Compound Nos. 1–48, were tested to evaluate their effectiveness in preventing or controlling powdery mildew disease of barley caused by the fungus *Erysiphe graminis* and powdery mildew disease of cucumber caused by the fungus, *Erysiphe cichoracearum*. This prevention or control capability was tested by utilizing the compounds of the present invention to control these diseases by systemic root uptake.

To accomplish this task, pots (4×4×3.5 inches) containing 10 plants of barley (Variety "Herta") and cucumber (Variety "Marketmore 70") were grown to age 6 days and 10 days, respectively. Upon reaching these ages, 45 ml. of emulsion compositions formed in accordance with Example 9 were added to each pot. That is, 48 pots were treated with emulsion compositions of the 48 compounds prepared in accordance with Examples 1 to 7. The 45 ml. compositions saturated the soil without significant loss through drainage into the saucers below the pots. In addition, a number of pots containing the same barley and cucumber plants were left untreated. These pots were used as controls.

Twenty-four hours after the treatment with the compositions of the present invention, both the barley and cucumber plants in all the pots, those treated and those untreated, were inoculated with powdery mildew fungus. This was accomplished by tapping leaves of previously infected barley and cucumber plants over the treated and untreated pots containing the barley and cucumber plants, respectively, to distribute spores of the fungus over the plants tested.

Six days after inoculation, disease control was evaluated on a 0 to 6 rating scale. A 0 rating was assigned when no disease was evidenced and a 6 rating was given for severe disease. Intermediate ratings were assigned depending on the degree of disease. Percent control was computed by comparing the ratings for the treated and untreated plants.

The results of this example, that is, the percent control for each of the compounds tested is reported in Table III. The results of the powdery mildew disease control of barley is reported under the title "BMS 250". The control of cucumber powdery mildew is similarly reported under the title of "CMS 250." It is noted that Table III appears after Example 16.

EXAMPLE 11

Control of Powdery Mildew in Barley by Foliar Application

Eight plants of "Larker" variety barley were planted in a pot. The number of pots were sufficient to accommodate testing in duplicate or triplicate pots for each of the 48 compounds tabulated in Table I. This number included a duplicate number of pots which acted as controls as will be discussed below.

Each of the compounds tabulated in Table 1 were tested by being sprayed onto the plants as compositions, prepared in accordance with Example 9, at a emulsion composition concentration of 1,000 mg/l. Compositions of each compound were sprayed on two or three pots. A number of pots were unsprayed and thus acted as controls. That is, for each pot sprayed an unsprayed pot was utilized as a control.

After the leaves of the sprayed pots were dried, they and the unsprayed control pots were placed in a greenhouse maintained at 21° C. All the pots were then inoculated with barley powdery mildew fungus, *Erysiphe graminis*. This inoculation was accomplished by distributing spores of the fungus over the leaves to be tested from plants which had previously been infected with the mildew disease.

Five days after inoculation, the plants were evaluated and assigned a disease rating of 0 to 6 as described in Example 10. Again, percent control was computed by comparing the treatment scores with the scores of the untreated controls. The results of these tests are summarized in Table III under the title "BMP 1000."

EXAMPLE 12

Control of Rice Blast Disease by Foliar Treatment

Five Bellemont rice plants were grown in a plurality of pots. The number of pots with planted rice plants were sufficient to test the compositions of all 48 compounds listed in Table I as well as controls therefor, the number of controls equal to the number of pots treated with each compound.

Three to four weeks after planting, the rice plants were sprayed with compositions of the compounds of this invention, prepared in accordance with Example 9. The concentration of each composition was 1,000 mg/l. An equal number of pots, also containing five rice plants per pot, remained unsprayed.

Sprayed and unsprayed pots of the plant were inoculated with spores of the rice blast fungus, *Pyricularia oryzae*. This inoculation was accomplished by preparing inoculum containing 20,000 to 30,000 spores per millilitre. The inoculum so prepared was sprayed on the plants with 1 to 2 drops of Tween [trademark]20 surfactant (ethoxylated sorbitan monolaurate) to insure proper wetting of the inoculum onto the plant leaves.

The plants were incubated in a controlled chamber at a humidity of 99% and a temperature of 21° C. for about 24 hours to allow infection to occur. The plants, after 24 hours in the control chamber, were transferred to a greenhouse for six days to permit disease development to occur. Disease was manifested by blast lesions on the leaves. Disease control was calculated by either counting lesions, if infection was moderate, or evaluating by the 0 to 6 rating system defined in Example 10. Of course, the evaluation system used in rating any of the compounds of the present invention was also utilized in evaluating its control. The results of this test are also tabulated in Table III under the title "RCB 1000."

EXAMPLE 13

Control of Bean Rust Fungus Eradicant Test

Pots were planted with two pinto bean plants, *P. vulgaris* each, susceptible to rust disease. When the plants were 7 days old, at the primary leaf stage of growth, they were all sprayed with a suspension containing 20,000 spores of the bean rust fungus, *Uromyces phaseoli*, per ml. All the pots containing the plants were than incubated in a controlled environmental chamber, maintained at 99% humidity and 21° C., for 24 hours to allow infection to occur. The plants were then removed from the incubator and allowed to dry. Two days after inoculation the infected plants were sprayed with compositions formed from the compounds of this invention, set forth in Example 9, at a dosage of 1,000 mg/l. A number of infected plants were not sprayed and acted as controls. All of the sprayed and unsprayed plants were then placed in a greenhouse at 21° C. for five days to allow any disease present to be expressed.

All the plants sprayed with the spore suspension were assessed for disease using the 0 to 6 rating system described in Example 10. Control of disease was determined by comparing treated plants with the untreated controls. The control of disease, expressed as percent reduction of disease, is included in Table III under the title "BRE 1000."

EXAMPLE 14

Control of Peanut Cercospora Leafspot by Foliar Treatment

Four Virginia peanut plants were grown in each of a plurality of pots. Enough pots were prepared so that the four plants in each of the pots could be sprayed with each of the compounds listed in Table I. This spraying occurred when the plants reached 4 weeks old. The 48 compounds of this invention were applied to the peanut plants by spraying emulsion compositions, prepared in accordance with the method employed in Example 9, in accordance with the method used in Example 10. The concentration of the emulsion compositions were 900 mg/l for each of the compounds listed in Table I. A number of pots containing four 4-week old Virginia peanut plants were left untreated to act as controls.

The treated (sprayed) and control (unsprayed) plants, after drying, were inoculated with spores of Peanut Cercospora leafspot, *Cercospora arachidicola*. The inoculum contained 20,000 to 30,000 spores per ml. The inoculum was sprayed with 1 to 2 drops of Tween [trademark] 20 surfactant (ethoxylated sorbitan monolaurate) to aid in wetting the leaves with the inoculum. All the inoculated peanut plant pots were incubated in a temperature-humidity control chamber at 24° C. for 36 hours to develop infection. The plants were than placed in a greenhouse for 21 days to allow disease development.

After 21 days in the greenhouse, all the plants were evaluated on the 0 to 6 disease rating system. Percent control was computed by comparing the scores of the treated pots and the untreated control pots. The results of this test are summarized in Table III under the title "PNT 900."

EXAMPLE 15

Control of Barley Blast

Pots were prepared such that they included 10 plants of 6 day old barley "Herta" variety. These pots were sprayed with compositions, formulated in accordance with the procedure of Example 9, of the compounds set forth in Table I. These pots, and a number of control pots planted with 10 "Herta" variety barley plants which were unsprayed, were inoculated with spores of the blast fungus, *Pyricularia oryzae*. In that *Pyricularia oryzae* is the same fungus utilized in Example 12, the method of inoculation was in accordance with the description given in that example.

All the inoculated pots were placed in a greenhouse maintained at a temperature of 21° C. and a humidity of 99% for five days. At that time, the plants were evaluated using the 0 to 6 disease rating scale. Percent control was computed by comparing the treatment scores of the treated and untreated pots. The results of this test are included in Table III under the title "BBL 1000."

EXAMPLE 16

Control of Nine Fungus Species

Compounds listed in Table I were solubilized in acetone at a concentration of 500 mg/l. That is, solutions were made of the compounds of the present invention such that there was 500 parts by weight of active compounds per million parts by volume of acetone. Filter paper discs, each 11 mm. diameter, were dipped in each of the test solutions. The discs were allowed to air dry to drive off the acetone solvent. A number of discs were untreated to provide controls.

The treated and untreated discs were then placed on agar plates and 8 fungus species: *Alternaria solani* (ALT), *Botrytis cinerea* (BOT), *Fusarium oxysporum* (FUS), *Helminthosporium maydis* (HMAY), *Phytophthora infestans* (PHY), *Sclerotinia sclerotiorum* (SCM) and *Sclerotium rolfsii* (SCO) were added to the center of each test disc in the form of a culture plug with the fungus mat in contact with the treated paper of the test disc. Two drops of a ninth fungi species, *Cercospora arachidicola* (CER), were added as a spore suspension (20,000 spores/ml) to the chemically treated test disc, rather than a mycelial culture plug. The plates were incubated at 29° C. in an oven and then the eight fungus species were evaluated by measuring the radius from the center of the fungus colony of the treated disc compared to the radius from the center of the fungus colony of the untreated discs.

Percent growth inhibition of each of the compounds tested was determined as a function of the difference between the radii of the treated and untreated discs for the eight fungus species.

In the case of the *Cercospora arachidicola* (CER) fungi, scoring was done on a numerical bases as follows:
100 = Complete inhibition of germination and growth.
80 = Nearly complete inhibition but some growth.
50 = Partial inhibition of growth or, early complete inhibition but later growth begins.
20 = Some inhibition of growth, but not significant.
0 = No inhibition of growth.

The results of all the above tests appear in Table III under the titles "ALT 500," "BOT 500," "FUS 500," "HMAY 500," "PHY 500," "CER 500," "SCM 500" and "SCO 500."

TABLE III

| | | | | | | | | | | | | PNT | RCB | SCM | SCO | BMP |
|---|---|---|---|---|---|---|---|---|---|---|---|---|---|---|---|---|
| | ALT | BBL | BMS | BOT | BRE | CER | CMS | FUS | HMAY | PHY | PMP | 900 | 1000 | 500 | 500 | 1000 |
| Cpd. | 500 | 1000 | 250 | 500 | 1000 | 500 | 250 | 500 | 500 | 500 | 1000 | (Ex | (Ex | (Ex | (Ex | (Ex |
| No. | (Ex 16) | (Ex 15) | (Ex 10) | (Ex 16) | (Ex 13) | (Ex 16) | (Ex 10) | (Ex 16) | (Ex 16) | (Ex 16) | (Ex 15) | 14) | 12) | 16) | 16) | 11) |
| 1 | 45 | 100 | 65 | 35 | 25 | 100 | 100 | 75 | 80 | 0 | 50 | 55 | — | 20 | 0 | — |
| 2 | 0 | 50 | 0 | 0 | 0 | 0 | 50 | 0 | 15 | 0 | 0 | — | — | 0 | 20 | — |
| 3 | 0 | — | 15 | 10 | 0 | 0 | 100 | 50 | 40 | 55 | 75 | — | — | 15 | 50 | — |
| 4 | 50 | 40 | 60 | 40 | 0 | 100 | 100 | 25 | 30 | 45 | 75 | — | — | 0 | 0 | 70 |
| 5 | 0 | 25 | 0 | 0 | 0 | 0 | 0 | 0 | 0 | 0 | 0 | — | — | 10 | 0 | 70 |
| 6 | 80 | 100 | 85 | 100 | 95 | 100 | 100 | 60 | 85 | 100 | 100 | — | — | 35 | — | 75 |
| 7 | — | — | 100 | — | — | — | 100 | — | — | — | — | — | — | — | — | — |
| 8 | 85 | 100 | 75 | 100 | 0 | 100 | 35 | 100 | 100 | 100 | 0 | — | — | 0 | 75 | 90 |
| 9 | 100 | 100 | 15 | 100 | 0 | 100 | 35 | 100 | 100 | 100 | 0 | — | — | 0 | 0 | 90 |
| 10 | 100 | 100 | 15 | 100 | 0 | 100 | 35 | 100 | 100 | 100 | 0 | — | — | 40 | 50 | 85 |
| 11 | 50 | 80 | 0 | 60 | 0 | 50 | 0 | 100 | 100 | 100 | 0 | — | — | 15 | 25 | 35 |
| 12 | 97 | 100 | 90 | 50 | 75 | 100 | 100 | 96 | 90 | 0 | 100 | 90 | 60 | 35 | 50 | — |
| 13 | 65 | 100 | 70 | 80 | 75 | 100 | 100 | 80 | 85 | 100 | 100 | — | — | 30 | 0 | 95 |
| 14 | 25 | 0 | 65 | 0 | 0 | — | 50 | 0 | 0 | 10 | 0 | — | — | 0 | 0 | 0 |
| 15 | 5 | 65 | 20 | 0 | 0 | 100 | 0 | 35 | 60 | 30 | 0 | — | — | 0 | 0 | 35 |
| 16 | 0 | 25 | 0 | 0 | 0 | 0 | 0 | 0 | 0 | 0 | 0 | — | — | 20 | 5 | 20 |
| 17 | 0 | 0 | 20 | 0 | 0 | 0 | 0 | 45 | 35 | 45 | 0 | — | — | 5 | 55 | — |
| 18 | 35 | 95 | 80 | 40 | 10 | 100 | 100 | 30 | 35 | 65 | 0 | — | — | 35 | 20 | 95 |
| 19 | 0 | 0 | 0 | 0 | — | 0 | — | 35 | 75 | 50 | 0 | — | — | 35 | 75 | — |
| 20 | 25 | 0 | 0 | 25 | 0 | 0 | 80 | 10 | 75 | 100 | 100 | — | — | 0 | 15 | 20 |
| 21 | 100 | 15 | 5 | 25 | 0 | 100 | 60 | 15 | 75 | 0 | 100 | — | — | 0 | 0 | 40 |
| 22 | 0 | 0 | 0 | 0 | 0 | 0 | 0 | 0 | 0 | 20 | 0 | — | — | — | — | 35 |
| 23 | 47 | 100 | 100 | 5 | 90 | 100 | 95 | 0 | 100 | 100 | 95 | 55 | 42 | 50 | 0 | 100 |
| 24 | 100 | 100 | 100 | 100 | 100 | 100 | 100 | 100 | 100 | 100 | 100 | — | — | 90 | 65 | 100 |
| 25 | 100 | 100 | 100 | 100 | 100 | 100 | 100 | 90 | 100 | 100 | 100 | — | — | 55 | 0 | 95 |
| 26 | 75 | 100 | 0 | 15 | 0 | 100 | 20 | 0 | 100 | 100 | 0 | 4 | — | 0 | 0 | 100 |
| 27 | 100 | 91 | 50 | 100 | 75 | 100 | 50 | 100 | 100 | 100 | 85 | 70 | 90 | 40 | 0 | 100 |
| 28 | 40 | 100 | 15 | 10 | 0 | 0 | 100 | 50 | 40 | 55 | 75 | — | — | 15 | 50 | 100 |
| 29 | 0 | 25 | 20 | 0 | 0 | 0 | 0 | 25 | 0 | 30 | 0 | — | — | 0 | 0 | 35 |
| 30 | 100 | 15 | 0 | 100 | 0 | 100 | 0 | 85 | 0 | 100 | 40 | — | — | 25 | 0 | 80 |
| 31 | 65 | 35 | 0 | 15 | 0 | 50 | 20 | 60 | 100 | 100 | 100 | — | — | 0 | 0 | 80 |
| 32 | 100 | 100 | 0 | 70 | 75 | 100 | 100 | 100 | 100 | 100 | 85 | — | — | 15 | 20 | 100 |
| 33 | 25 | — | 20 | 0 | 0 | 0 | 0 | 35 | 15 | 50 | 0 | — | 80 | 0 | 15 | 35 |
| 34 | 45 | — | 90 | 0 | 90 | 0 | 90 | 35 | 45 | 90 | 100 | — | 60 | 35 | 30 | 35 |
| 35 | 15 | 0 | 100 | 25 | 0 | 0 | 100 | 15 | 65 | 55 | 50 | — | — | 0 | 0 | 0 |
| 36 | 100 | 100 | 20 | 100 | 60 | 100 | 20 | 100 | 100 | 100 | 0 | — | 0 | 20 | 0 | 100 |
| 37 | 10 | 60 | 65 | 0 | 0 | 0 | 75 | 10 | 65 | 15 | 0 | — | — | 0 | 10 | 35 |
| 38 | 35 | 80 | 0 | 10 | 0 | 50 | 40 | 25 | 85 | 50 | 0 | — | — | 0 | 0 | 65 |
| 39 | 75 | 20 | 0 | 75 | 0 | 100 | 0 | 70 | 100 | 100 | 0 | — | — | 0 | 0 | — |
| 40 | 0 | 15 | 60 | 0 | 0 | 0 | 60 | 0 | 0 | 15 | 0 | — | — | 0 | 0 | 80 |
| 41 | 60 | 100 | 100 | 0 | 100 | 100 | 100 | 60 | 100 | 100 | 60 | — | — | 0 | 0 | 100 |
| 42 | 100 | — | 80 | 100 | 100 | 100 | 15 | 100 | 100 | 100 | 100 | — | 100 | 0 | 0 | 100 |
| 43 | 100 | — | 40 | 100 | 100 | 100 | 15 | 100 | 100 | 100 | 100 | — | 100 | 70 | 25 | 100 |
| 44 | 100 | — | 80 | 100 | 100 | 100 | 65 | 100 | 100 | 100 | 100 | — | 100 | 40 | 0 | 100 |
| 45 | 20 | — | 60 | 0 | 75 | 0 | 40 | 50 | 60 | 75 | 60 | — | 100 | 0 | 0 | 85 |
| 46 | 0 | — | 60 | 0 | 90 | 0 | 80 | 0 | 40 | 10 | 100 | — | 80 | 0 | 0 | 50 |
| 47 | 35 | — | 90 | 50 | 0 | 100 | 80 | 50 | 75 | 50 | 25 | — | 0 | 0 | 0 | 75 |
| 48 | 0 | — | 65 | 50 | 0 | 0 | 15 | 40 | 35 | 35 | 0 | — | 85 | 0 | 0 | 50 |

EXAMPLE 17

Growth Regulation of Soybean, Cotton, Bean and Barley Plants

Aqueous compositions of Compound Nos. 1, 3, 4, 6, 7, 9, 10, 12, 13, 18–25, 27, 28, 30, 31, 35, 41, 44, 45, 47 and 48 were prepared in accordance with the procedure set forth in Example 9. In particular, these compositions were prepared in concentrations of 1,000 mg/l and 3,000 mg/l from 450 mg. of the compound dissolved or dispersed in 10 ml. distilled water or an organic solvent, usually acetone, to which 20 mg. of an emulsifying agent, usually ethoxylated sorbitan monolaurate (Tween [trademark] 20), was added. The solution or dispersion was diluted to 150 ml. with distilled water, producing a 3,000 mg/l aqueous composition. By appropriate further dilution with distilled water, a 1,000 mg/l aqueous composition was prepared.

The compositions, prepared in accordance with the above procedure, were atomized with a DeVilbiss [trademark] No. 152 sprayer onto the foliage of soybean plants (*Glycine max* (L.) Merr. cv. Williams, 2 weeks old), cotton plants (*Gossypium hirsutum* L. cv. Stoneville 213, 3 to 4 weeks old), bean plants (*Phaseolus vulgaris* L. cv. Pinto III, 2 weeks old) and barley plants (*Hordeum vulgare* L. cv. Herta, 1 week old). Spraying continued until the foliage was wetted to the drip point. After 1 to 3 weeks, depending on the plant species, the plants were evaluated for retardation of vegetative growth as against untreated controls.

The results of this plant growth test, in which the soybean, cotton and barley plants were treated with 3,000 mg/l of the tested compounds and the bean plants were treated with the same compounds at a concentration of 1,000 mg/l, are summarized in Table IV.

TABLE IV

| | Percent Growth Retardation | | | |
|---|---|---|---|---|
| Cpd. No. | Bean (1000 mg/l) | Barley (3000 mg/l) | Cotton (3000 mg/l) | Soybean (3000 mg/l) |
| 1 | 0 | 0 | 95 | 100 |
| 3 | 30 | 0 | 20 | 20 |
| 4 | 40 | 0 | 0 | 90 |
| 6 | 95 | 0 | 50 | 90 |

TABLE IV-continued

| Cpd. No. | Percent Growth Retardation | | | |
|---|---|---|---|---|
| | Bean (1000 mg/l) | Barley (3000 mg/l) | Cotton (3000 mg/l) | Soybean (3000 mg/l) |
| 7 | 80 | 0 | 90 | 100 |
| 9 | 40 | 0 | 0 | 90 |
| 10 | 60 | 0 | 20 | 0 |
| 12 | 100 | 0 | 90 | 100 |
| 13 | 95 | 0 | 20 | 30 |
| 18 | 0 | 0 | 0 | 95 |
| 19 | 0 | 0 | 100 | 0 |
| 20 | 50 | 0 | 30 | 100 |
| 21 | 50 | 0 | 40 | 50 |
| 23 | 75 | 0 | 40 | 100 |
| 24 | 30 | 0 | 30 | 100 |
| 25 | 80 | 0 | 80 | 95 |
| 27 | 50 | 0 | 0 | 20 |
| 28 | 20 | 0 | 0 | 0 |
| 30 | 0 | 0 | NT | 30 |
| 31 | 0 | 0 | NT | 50 |
| 35 | 60 | 0 | 100 | 100 |
| 41 | 90 | 0 | NT | 0 |
| 44 | 50 | 0 | NT | 0 |
| 45 | 50 | 0 | NT | 0 |
| 47 | 0 | 0 | NT | 30 |
| 48 | 20 | 0 | NT | 0 |

NT = Not Tested

The above embodiments and examples are given to illustrate the scope and spirit of the instant invention. These embodiments and example will make apparent, to those skilled in the art, other embodiments and examples. These other embodiments and examples are within the contemplation of the present invention. Therefore, this inventin should be limited only by the appended claims.

What is claimed is:

1. A compound having the structural formula

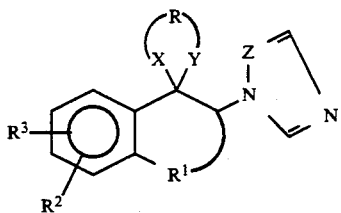

where

R is $C_2-C_8$ alkylene having 2 to 4 carbon atoms linking X and Y;

$R^1$ is $C_1-C_8$ linear or branched alkylene, $R^2$ and $R^3$ are the same or different and are hydrogen, halogen, $C_1-C_8$ alkyl, $C_1-C_6$ alkoxy, $C_1-C_6$ alkylthio, $C_1-C_6$ alkylsulfonyl, phenyl, phenoxy, cyano, nitro, $-OCOR^4$, $-COOR^5$, $-CH_mQ_{3-m}$ or $-OCH_mQ_{3-m}$;

$R^4$ is $C_1-C_4$ alkyl;

$R^5$ is hydrogen or $C_1-C_4$ alkyl;

Q is halogen;

X and Y are the same or different and are oxygen, sulfur, sulfinyl, or sulfonyl

Z is nitrogen and m is 1, 2 or 3;

or physiologically acceptable salts thereof.

2. A compound in accordance with claim 1 wherein R is $-(CH_2)_n-$, $-CH_2CH(R^6)-$ or $-CH(CH_3)CH(CH_3)-$;

$R^1$ is $C_1-C_3$ alkylene, $R^2$ and $R^3$ are the same or different and are hydrogen, halogen, $C_1-C_4$ alkyl, $C_1-C_4$ alkoxy, $C_1-C_4$ alkylthio, $C_1-C_4$ alkylsulfonyl, phenyl, phenoxy, cyano or nitro;

$R^6$ is $C_1-C_6$ alkyl;

X and Y are the same or different and are oxygen, sulfur, sulfinyl or sulfonyl, and n is 2 or 3;

or physiologically acceptable salts thereof.

3. A process for controlling phytopathogenic fungi comprising applying a fungicidally effective amount of the compound of claim 1 to the locus under attack by said fungi.

4. A process for controlling phytopathogenic fungi comprising applying the compound of claim 1, at a concentration of 10 ppm to 500 ppm, to the soil in which plants to be protected from phytopathogenic fungi are grown.

5. A process for controlling phytopathogenic fungi comprising applying the compound of claim 1 as a coating to seeds of plants to be protected from phytopathogenic fungi at a coating concentration of 5 to 75 grams of the compound of claim 1 per 100 kg. of seed.

6. A process for regulating plant growth comprising applying a plant growth regulant effective amount of the compound of claim 1 to the plant whose growth is to be regulated.

7. A fungicidal composition comprising a fungicidally effective amount of the compound of claim 1 and an inert carrier therefor.

8. A plant growth regulant composition comprising a plant growth regulant effective amount of the compound of claim 1 and an inert carrier therefor.

* * * * *